United States Patent [19]

Gotthard

[11] Patent Number: 4,551,266
[45] Date of Patent: Nov. 5, 1985

[54] TREATMENT OF SUBSTANTIALLY METALLIC ION FREE ACRYLAMIDE AND RELATED COMPOUNDS

[75] Inventor: George Gotthard, Short Hills, N.J.

[73] Assignee: American Cyanamid Company, Stamford, Conn.

[21] Appl. No.: 570,402

[22] Filed: Jan. 4, 1984

Related U.S. Application Data

[63] Continuation of Ser. No. 362,365, Mar. 26, 1982, abandoned, which is a continuation-in-part of Ser. No. 258,103, Apr. 27, 1981, abandoned.

[51] Int. Cl.$^4$ .............................................. C09K 15/32
[52] U.S. Cl. ................................ 252/400 R; 526/196; 526/303.1; 526/317.1
[58] Field of Search ............... 526/77, 197; 252/400.4, 252/400.41; 562/600; 564/203

[56] References Cited

U.S. PATENT DOCUMENTS 3,951,600  4/1976  Asano ..................................... 526/77
4,167,616  9/1979  Bollinger ............................. 526/197

Primary Examiner—Christopher A. Henderson
Attorney, Agent, or Firm—John W. Cornell

[57] ABSTRACT

Acrylamide and related monomers which are substantially free of any metallic ions and contain only that amount of oxygen or other polymerization inhibitor which is inherently present in the monomer are improved by adding thereto a borane compound, i.e., sodium borohydride.

8 Claims, No Drawings

TREATMENT OF SUBSTANTIALLY METALLIC ION FREE ACRYLAMIDE AND RELATED COMPOUNDS

CROSS-REFERENCE TO RELATED APPLICATIONS

This application is a continuation of application Ser. No. 362,365, filed Mar. 26, 1982, now abandoned, which is in turn a continuation-in-part of application Ser. No. 258,103 filed Apr. 27, 1981, now abandoned.

This invention relates to the treatment of acrylamide and related monomers in the form of 5 to 20 weight percent aqueous solutions which are substantially free of metallic ions and contain only that amount of oxygen or other polymerization inhibitor which is inherently present in the monomer so as to be able to produce water-soluble high molecular weight synthetic polymers, especially when the monomers contain an unacceptably high level of impurities which result in poor polymer products having, for example, excessive amounts of insolubles and/or unacceptably low viscosities and/or low rates of polymerization. More specifically, it relates to the use of a borane compound which contains at least one —B—H moiety to treat 5 to 20 weight percent aqueous acrylamide and/or acrylic acid solutions which are essentially free of metallic ions but contain other impurities to produce polymers of acrylamide and/or acrylic acid which are essentially the same as those polymers prepared from especially pure monomers.

Acrylamide is conventionally prepared by the hydration of acrylonitrile as is well-known in the art. This material generally exits the process as a concentrated (30 to 60% by weight) aqueous solution. Acrylic acid is conventionally prepared by the oxidation of propylene as is well-known in the art. This material generally is available as concentrated aqueous solutions, i.e., 60% to glacial. For economical reasons, it is extremely desirable that these products be directly polymerized to water-soluble, high molecular weight products. However, these monomer solutions or powders apparently contain unknown impurities at the level of parts per million, the exact amount or type being undetermined to date. When such monomers are polymerized, even with this very low level of impurities present, quite often totally unacceptable polymers result.

In solution polymerizations, attempts at solving these problems required any or all of: (a) very low polymer drying temperatures; (b) extensive and expensive purification of the monomer solution by recrystallization; (c) very long polymerization times; (d) addition of very large amounts of urea or chain transfer agents to the monomer; (e) polymerizing in very dilute solutions and (f) adding post-polymerization stabilizers. However, each of these has been found unsatisfactory for large scale commercial use due to being either energy-intensive or expensive in that the rate of production of polymers is drastically curtailed or the percent of desired polymer is reduced to an unacceptable level.

In water-in-oil emulsions, attempts at solving these problems entail: (a) monomer purification by recrystallization; (b) polymerizing very dilute solutions; (c) use of different initiators; (d) addition of urea to the monomer, and/or (e) use of chain transfer agents. However, these have also been found unsatisfactory for the same or similar reasons as above.

In U.S. Pat. No. 2,963,459, there is disclosed the use of metal borohydrides as catalysts for aqueous emulsion polymerization. Defensive Publication No. T 875,006 discloses the use of alkali metal and alkaline earth metal borohydrides as catalysts to control the steric configuration and physical properties in the bulk or solution polymerization of acrylic monomers.

Accordingly, developments that could purify impure monomers readily and result in polymers therefrom of greater molecular weight or viscosity with minimum amounts of insolubles therein would fulfill a long-known need and constitute a notable advance in the art.

In accordance with the present invention, there is provided a composition comprising (a) a monomer of inferior polymerizability selected from acrylamide, acrylic acid and mixtures thereof, said monomer being in the form of a 5 to 20 weight percent aqueous solution, substantially free of any metallic ion and containing only that amount of oxygen or other polymerization inhibitor which would inherently be present in said monomer, and (b) a borane compound containing at least one —B—H moiety selected from borohydrides and complexes or boron hydrides, optionally on a resinous support.

In accordance with the present invention, there is also provided a process for improving the polymerizability of a monomer of inferior polymerizability selected from acrylamide, acrylic acid and mixtures thereof, said monomer being in the form of a 5 to 20 weight percent aqueous solution, substantially free of any metallic ion and containing only that amount of oxygen or other inhibitor which would normally be present in said monomer, which comprises treating said monomer with an effective amount of a borane compound having at least one —B—H moiety selected from borohydrides and complexes of boron hydrides for a sufficient time to provide a monomer of improved polymerizability.

There is still further provided a process for producing a water-soluble high molecular weight polymer by polymerizing a monomer of inferior polymerizability selected from acrylamide, acrylic acid, and mixtures thereof as a 5 to 20 weight percent aqueous solution, said monomer being substantially free of any metallic ion characterized by treating said monomer with a borane compound containing at least one —B—H moiety prior to polymerization.

There is also provided a process for producing a water-soluble high molecular weight polymer by polymerizing a monomer of inferior polymerizability selected from acrylamide, acrylic acid and mixtures thereof as a 5 to 20 weight percent aqueous solution said monomer being substantially free of any metallic ion and drying the resultant polymer characterized by treating said polymer after polymerization and prior to drying with a borane compound containing at least one —B—H moiety and selected from borohydrides and complexes of boron hydrides.

In accordance with the present invention, the borane treatment of monomers of inferior polymerizability enables polymers to be provided that have higher viscosity and lower amounts of insolubles than corresponding polymers made from untreated monomers of inferior polymerizability.

By the expression "improving the polymerizability of a monomer of inferior polymerizability", as that term is used herein and in the appended claims, is meant providing a monomer which produces a polymer of higher molecular weight, as indicated by standard viscosity, than does the corresponding monomer of inferior polymerizability, produces a polymer containing less insolubles than does the corresponding monomer of inferior polymerizability or provides both higher viscosity and lower insolubles.

The compounds used herein to produce improved monomers are those compounds which contain at least one —B—H moiety. These compounds are referred to as boranes. Generally, these compounds are catalysts or parts of catalyst systems for the polymerization of acrylamide and/or acrylic acid but under the substantially metal free conditions herein, they do not cause such polymerization except after extended times.

These compounds may be borohydrides or complexes of boron hydrides with other compounds.

Examples of borohydrides useful herein include, but are not limited to: the borohydrides (tetrahydroborates) of sodium, potassium, rubidium, cesium, calcium, barium, strontium, magnesium, thorium, mercury, gold, and lead; the cyanoborohydrides of the above metals; Lalancette's Reagent ($NaBH_2S_3$); hydridotrialkoxyborates of the above metals; tetramethyl ammonium octahydrotriborate as well as other hydropolyborates, e.g. salts of $B_{12}H_{12}^{-2}$ and the like. Preferably, the alkali metal borohydrides are used. Most preferably, sodium borohydride is used due to its commercial availability.

Examples of complexes of boron hydrides with other compounds include the amine boranes wherein amines are combined with tetrahydroborates. Suitable such amines include ammonia, methylamine, dimethylamine, trimethylamine, triethylamine, isopropylamine, diisopropylamine, t-butylamine, N,N-dimethyl-2-methoxyethylamine, pyridine, piperazine, morpholine, methylmorpholine, 2,6-lutidine, methoxypyridine, 4-aminopyridine, and the like.

Alternatively, the borane compound may be supported on a resin or used as a counterion on a quaternary ion exchange resin or as commercially available Amborane ® resins of Rohm and Haas, or amine polymers which are reacted with borohydrides e.g. poly(4-vinylpyridine)borane.

Any borane compound to be useful herein must, of course, have sufficient stability in the monomer to overcome the detrimental effects of the impurities.

The acrylamide, acrylic acid or mixture thereof used herein are any which are substantially free of metallic ion, such as cuprous, cupric, ferrous, and ferric ions which could form an initiator system in the presence of a borane compound. The metals which may either be present due to the manufacture of the monomer or due to being intentionally added to inhibit polymerization may be best removed by passing the monomer through an effective cation exchange resin. In addition, the monomers have not been intentionally deaerated, i.e., they contain only the amount of entrapped oxygen that would be expected. The monomers are used as about 5 to 20 weight percent aqueous solutions, preferably about 8 to 15 weight percent.

To perform the treatment herein and incorporate the borane compound into the monomer, the borane compound is simply added thereto preferably in the form of a solution or powder with stirring.

For the use of sodium borohydride, the pH during at least a portion of the treatment should be above 8 and preferably above 10. These pH values may be obtained by the addition of a base such as a caustic to the monomer or by merely increasing the amount of sodium borohydride used as it is itself very basic.

The amount of borane compound to be used in accordance with the present invention has been found to depend, at least in part, upon the type of polymerization the monomer may substantially undergo, the pH of the monomer being treated, the amount of impurities in the monomer being treated, the presence or absence of urea during polymerization and the amount thereof, and the time allowed for the treatment, as well as the concentration of the monomer solution being treated. As such, an exact "monomer improving amount" cannot be defined. Generally, however, it will range from about 50 parts per million to 2 weight percent, based upon the monomer. When the monomer is to be used for water-in-oil emulsion polymerizations, generally larger amounts of the borane should be used while the smaller amounts have been found to suffice for solution polymerizations. Preferably about 50 to 5000 parts per million are used and most preferably about 100 to 2000 parts per million.

Generally the treatment time may be from minutes to hours, with the time a function of the amount of borane used. Thus, suitable treatment times may range from about 5 minutes to 8 hours. A treatment time of about one-half to two hours with a borane content of about 250 parts per million on a 10 weight percent acrylamide solution which is pH adjusted to 10 prior to adding the borane has been found suitable for making a solution polymerized polyacrylamide.

After the treatment, any excess borane compound may be removed by passing the monomer solution through a column which will attract the borane compound or preferably, it may be decomposed to the corresponding borate by the addition of an acid. This reaction liberates hydrogen and hence should be done with proper safety precautions. Thus, the use of dilute acids for relatively extended times are preferred. Suitable acids include sulfuric, phosphoric, hydrochloric and the like. They should be used at about 5 to 20 weight percent solution with the addition taking from at least 15 minutes, preferably about 30 minutes, up to about an hour. Although shorter times and higher concentrations may be used, there is an increased risk of unwanted, uncontrolled premature polymerization of the monomer. During the acidification, the hydrogen gas content of the air should be maintained at below 4%. Alternatively, an extended treatment time of up to several days without acidification may be allowed for the borane to slowly hydrolyze to the corresponding borate.

The process of treating the impure monomer may be conducted in a continuous manner, if desired. In this procedure, the monomer in solution form is fed to a first reactor along with suitable treating agent while sparging with air. The solution plus treating agent with air sparge continuing is then transferred to a second reactor to provide adequate reaction time. The solution is then transferred to an additional reactor where it is treated with acid to decompose excess treating agent while maintaining air sparging.

Even following the above borane treatment, it has sometimes been found advantageous to incorporate into the polymerization recipe up to about 20 weight percent, based on the monomer, of urea or a urea derivative. Generally, 5 to 10 weight percent of urea itself is used. Suitable compounds are disclosed in U.S. Pat. No. 3,622,533.

Copolymers of the above-named monomers or of one or more of the named monomers with other ethylenically-unsaturated monomers suitable to produce water-soluble products may also be prepared. Such other monomers include, but are not limited to, methacrylamide, salts of acrylic acid, methacrylic acid and its salts, methyl acrylate, ethyl acrylate, propyl acrylate, methyl methacrylate, ethyl methacrylate, dimethylaminoethyl acrylate, dimethylaminoethyl methacrylate, diethylaminoethyl acrylate, hydroxyethyl acrylate, hydroxyethyl methacrylate, diethylaminoethyl acrylate methylsulfate quaternary salt, styrene, acrylonitrile, 3-(methacrylamido)-propyl-trimethyl ammonium chloride, vinyl methyl ether, vinyl ethyl ether, alkali metal and ammonium salts of vinyl sulfonic acid, and the like. All or part of the acrylamide portion of the polymers may be hydrolyzed.

The polymerization method to be used with the treated monomer is any which is conventionally used to polymerize such monomers. This specifically includes solution and emulsion polymerizations, although other techniques such as bead and suspension or dispersion polymerizations may be used. The particular polymerization system for each of these is that which is conventionally used. For solution polymerization this generally entails using one or more azo-initiators with or without a redox system, and optionally such conventional additives as sequesterants, alcohols and diluents as necessary to the polymerization. For emulsion polymerization, which is a water-in-oil emulsion, this entails using a water-in-oil emulsifying agent, an oil phase such as toluene, xylene, or a paraffinic oil, and a free radical initiator.

As the present invention is independent of the particular polymerization method, further details thereon may be readily found in the literature. Furthermore, the quantities and the individual components will vary according to the monomers polymerized and the process conditions under which the polymerization is to occur.

Moreover, the advantages of the present invention may also be realized by adding the borane compound not to the monomer as a treatment, but rather to the resulting polymeric gel before drying thereof. This is not as desirable in that there may be great difficulty in uniformly mixing the borane into the gel and hydrogen gas is evolved in the drier. This shows that however the borane is operating, it seems to also work during the drying of a solution polymer.

The following specific examples illustrate certain aspects of the present invention and more particularly point out the benefits obtained thereby. However, the examples are set forth for illustration only and are not to be construed as limitations on the present invention except as set forth in the appended claims. All parts and percentages are by weight unless otherwise specified.

EXAMPLE 1

Treatment of Ion-Exchanged Acrylamide with NaBH₄

(a) Acrylamide 50% aqueous which contains about 25 ppm copper and other conventional impurities found in acrylamide is passed through an ion-exchange column containing a cation exchange resin (Amberlite ® IR-120 of Rohm and Haas). The material exiting the column contains less than about 0.6 ppm copper.

A portion of the above acrylamide is diluted to about 10% by the addition of distilled water and 5000 grams (g) thereof is placed in a glass beaker and 0.5 g (1000 ppm) of sodium borohydride powder is added with minimal stirring. Thereafter the mixture is stored overnight without polymerizing.

(b) When the above procedure is repeated on acrylamide which has not been passed through an ionexchange column, the mixture polymerizes within minutes.

Comparative Example

The procedure of Example 1(a) is repeated except that the acrylamide 50% aqueous contains 0.7 ppm copper and it is not diluted prior to the addition of sodium borohydride. The borohydride is added in increments of about 35 ppm borohydride based upon the monomer allowing about 15 minutes between each increment. About 10 minutes after the borohydride concentration reached 250 ppm, the solution polymerized.

EXAMPLE 2

Solution Polymerization of Monomer of Example 1(a)

The monomer solution of Example 1(a) in which any excess borane compound is decomposed with sulfuric acid and the solution then neutralized is solution polymerized as follows: 3160 g of a 10.43% aqueous acrylamide monomer solution is placed in a reaction vessel and magnetically stirred. The following are subsequently added with the stirring continued:

16 g anhydrous sodium sulfate
16 g urea
4 ml 4.5% aqueous ethylenediamine tetraacetic acid When the solution is complete, the pH of the reaction mass is adjusted to 6.0 with sulfuric acid. A nitrogen purge is started at about 250 ml per minute for 30 minutes while warming the reaction mass to about 35° C. With the nitrogen purge continuing, polymerization commences within minutes after the introduction of the catalysts:

500 ppm of 2,2'-azobis(2-amidinopropane)-dihydrochloride

The polymerization is allowed to continue substantially adiabatically by insulating the reaction vessel. The polymerizate is allowed to experience a 23.3° C. exotherm over about a two-hour period. Thereafter the reaction continues for about 18 hours producing about 3000 grams of a stiff gel product.

The gel is subsequently cut into slivers and dried in a convection oven for 4 hours at 85° C. to have residual volatiles of 7 to 10%. The dried product is reduced in particle size in a Waring Blender and screened to yield product at a −20 U.S. mesh particle size.

EXAMPLE 3

Evaluation of Product of Example 2

To evaluate the product prepared in Example 2, the following is done:

0.3 gram of the dried product is dissolved in deionized water to produce 300 grams of about 0.1% aq. polymer solution. The solution is passed through a 100 U.S. mesh weighed screen to filter out any insolubles. The screen is washed with about 500 ml deionized water at room temperature and dried at 100° C. overnight before determination of the amount of insolubles which is reported as percent.

The "as is" standard viscosity is determined by dissolving 0.3 grams of product in deionized water over 2 hours to yield a 300 gram aqueous solution, filtering out the insolubles through a U.S. 100 mesh screen and then adding enough sodium chloride to form a 1 Molar NaCl solution and determining the Brookfield viscosity using a UL (ultra low) adaptor. This is indicative of the performance of the resultant product in that the higher the number, the more desirable is the product.

The results, along with those for a comparison prepared by the same procedure but wherein no sodium borohydride is used, are:

|  | Example 2 | Comparison |
|---|---|---|
| "As Is" Standard Viscosity, cps. | 3.8 | 3.0 |
| % Insolubles | 0.7 | 7.6 |

The results clearly demonstrate that by treating the ion-exchanged acrylamide with sodium borohydride, the "as is" viscosity is greatly increased and the percent insolubles greatly reduced.

EXAMPLE 4

The procedure of Example 2 is repeated except for varying the concentration of sodium borohydride, limiting the contact time to 2 hours, and reducing the catalyst concentration to 375 ppm based on acrylamide. The results of testing in accordance with Example 3 are:

| NaBH$_4$/AMD ppm | "As Is" Standard Viscosity cps | % Insolubles |
|---|---|---|
| 0 | 1.9 | 75 |
| 36 | 2.1 | 49 |
| 72 | 2.0 | 84 |
| 107 | 2.0 | 62 |
| 143 | 2.1 | 17 |
| 1000 | 3.5 | 0.1 |

EXAMPLE 5

The procedure of Example 4 is repeated except that the pH of the acrylamide solution is adjusted to 10 prior to the addition of the sodium borohydride. The results are:

| NaBH$_4$/AMD ppm | "As Is" Standard Viscosity cps | % Insolubles |
|---|---|---|
| 0 | 1.9 | 75 |
| 100 | 3.7 | — |
| 150 | 3.5 | — |
| 250 | 3.8 | 0.5 |
| 500 | 3.7 | 0.5 |
| 750 | 3.6 | 0.8 |
| 1000 | 3.5 | 0.5 |

The results of Examples 4 and 5 demonstrate that sufficient borohydride must be present at the operative pH range (pH about 10 for sodium borohydride) to improve the polymer. At the lower levels in Example 4 such is not the case. They further demonstrate that an excess is not found to be detrimental.

EXAMPLE 6

Treatment of Ion-Exchanged Acrylamide with Amborane ® Resin

Acrylamide 50% aqueous as in Example 1(a) is passed through an ion-exchange column and has less than 0.5 ppm copper. Thereafter, it is diluted to about 10% and mixed with varying amounts of Amborane ® 355 (a resin containing numerous amine-borane groups) of Rohm and Haas for 2 hours. During this treatment the pH is continually adjusted to be in the range of 5.5–6.5. Then the various treated acrylamides tested as in Example 2. The treatments and results are as shown in Table I below.

TABLE I

| RESULTS OF EXAMPLE 7 | | | |
|---|---|---|---|
| Acrylamide 50%, g | Amborane ® 355, g | "As Is" Stardard Viscosity, cps | % Insolubles |
| 700 | 53 | 3.2 | 0.1 |
| 700 | 10.5 | 3.8 | 0.7 |
| 700 | 7 | 3.3 | 2.6 |
| 700 | 3.5 | 2.9 | 28.0 |
| 700 | — | 2.5 | 38.0 |

EXAMPLE 7

The procedure of Example 2 is repeated wherein no pretreatment with sodium borohydride is made. After the polymerization and prior to drying, 0.5% sodium borohydride powder was mixed into a portion of the polyacrylamide and the final properties are determined to be:

| NaBH$_4$ | "As Is" Standard Viscosity cps | % Insolubles |
|---|---|---|
| Yes | 3.5 | 0.6 |
| No | 2.6 | 14.6 |

Thus it is apparent that the borohydride treatment is equally effective when it is performed prior to polymerization or merely prior to drying.

EXAMPLE 8

The basic procedure of Example 2 is repeated except that 10% by weight of the acrylamide is replaced by an equivalent weight of each of the following monomers in separate runs:

(a) acrylic acid
(b) 2-acrylamido-2-methylpropane ammonium sulfonate
(c) Dimethylaminoethylmethacrylate methyl sulfate quaternary salt For (a) and (b) the pH is adjusted with sodium hydroxide.

Comparable improved results over those same copolymers prepared from untreated acrylamide are observed.

EXAMPLE 9

Use of Other Borohydrides

The procedures of Examples 1(a) and 2 are repeated except that the sodium borohydride is replaced by the following compounds:

Sodium cyanoborohydride
Potassium borohydride

Similar improved results are observed with these compounds as compared to those obtained with untreated monomers.

What is claimed is:

1. A composition comprising:
   (a) a monomer of inferior polymerizability selected from acrylamide, acrylic acid and mixtures thereof, said monomer being in the form of a 5 to 20 weight percent aqueous solution having a pH above 8.0, substantially free of any metallic ion and containing only that amount of oxygen or other polymerization inhibitor which would inherently be present in said monomer; and (b) a monomer-improving amount, insufficient to catalyze polymerization of said monomer of an alkali metal borohydride compound, said borohydride compound being present at about 100 parts per million to about 1000 parts per million based upon the monomer.

2. The composition of claim 1 wherein the monomer improving amount of component (b) is effective to provide the product produced by polymerization of said monomer (a) with reduced insolubles content, as compared with the product produced by polymerization of monomer (a) in the absence of (b).

3. The composition of claim 1 wherein the alkali metal borohydride compound is sodium borohydride.

4. The composition of claim 1 further containing at least one additional ethylenically-unsaturated monomer capable of being copolymerized therewith to form a water soluble copolymer.

5. The composition of claim 4 wherein the further monomer is selected from the group consisting of acrylic acid or a salt thereof, 3-(methacrylamido)-propyltrimethyl ammonium chloride, dimethylaminoethylmethacrylate methyl sulfate quaternary salt and acrylonitrile.

6. The composition of claim 1 wherein said monomer is acrylamide.

7. The composition of claim 6 wherein the acrylamide monomer is an aqueous solution containing about 8 to 15 weight percent acrylamide monomer.

8. The composition of claim 1 wherein said monomer is acrylic acid or a salt thereof.

* * * * *